United States Patent [19]

Flax

[11] Patent Number: 4,546,772

[45] Date of Patent: Oct. 15, 1985

[54] METHOD AND MEANS FOR DETERMINING ULTRASONIC WAVE ATTENUATION IN TISSUE USING PHASE LOCKED LOOP

[75] Inventor: Stephen W. Flax, Waukesha, Wis.

[73] Assignee: General Electric Company, Milwaukee, Wis.

[21] Appl. No.: 520,958

[22] Filed: Aug. 8, 1983

[51] Int. Cl.⁴ ............................................. A61B 10/00
[52] U.S. Cl. ..................................... 128/660; 73/599
[58] Field of Search ................................ 128/660–663; 73/597, 599, 602, 625–626

[56] References Cited

U.S. PATENT DOCUMENTS

| 4,016,750 | 4/1977 | Green | 73/599 X |
| 4,202,215 | 5/1980 | Meyer | 128/660 X |
| 4,389,893 | 6/1983 | Ophir et al. | 73/599 |
| 4,414,850 | 11/1983 | Miwa et al. | 128/660 X |
| 4,446,740 | 5/1984 | Wilson et al. | 128/660 X |

OTHER PUBLICATIONS

Pan, K. M. et al., "Tomographic Reconstruction of Ultrasonic Attenuation with Correction for Refractive Errors", IBM Jrnl. Res. & Devel., Jan. 1981, pp. 71–82.
Kac, R. et al., "Estimating the Acoustic Attenuation Coeff. Slope for Liver from Reflected UTS Signals," IEEE Trans. Sonics & Ultrasonics, vol. SU–26 #5, Sep. 1979, pp. 353–362.
Atherton, J. P. *PLL Article,* IEEE Proc. vol. 129, Part A, No. 6, Aug. 1982, pp. 396–398.
Stagg, J. et al., "Electronic Analysis of Fetal Breathing Movements: A Practial Application of PLL Principles", Jrnl. of Med. Eng. & Tech., vol. 2, #5, Sep. 1978, pp. 246–249.
Dines, K. A. et al., "UTS Attenuation Tomography of Soft Tissues", UTS Imaging, vol. 1, #1, 1979, pp. 16–33.

*Primary Examiner*—Kyle L. Howell
*Assistant Examiner*—Francis J. Jaworski
*Attorney, Agent, or Firm*—Flehr, Hohbach, Test, Albritton & Herbert

[57] ABSTRACT

The frequency of a reflected ultrasonic wave decreases in frequency as the wave is attenuated in passing through tissue. A measure of attenuation is obtained by applying an electrical signal generated from the ultrasonic wave to a phase detector along with a signal from a voltage controlled oscillator and controlling the voltage controlled oscillator with the output of the phase detector. By measuring the voltage applied to control the oscillator, an estimation of the mean frequency (first moment) of the power spectrum is obtained. This frequency estimator can, in turn, be used to estimate the attenuation of the ultrasonic wave as it propagates through the media by noting the shift in frequency with propagation depth.

3 Claims, 1 Drawing Figure

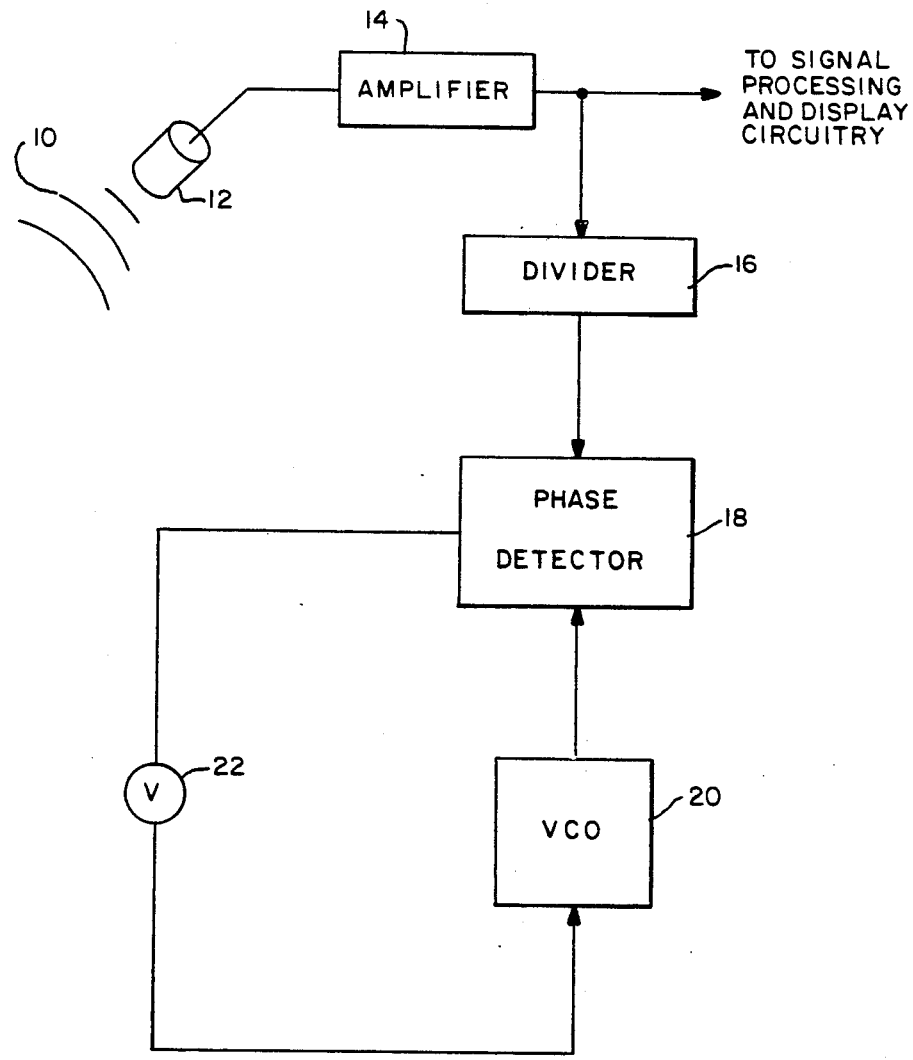

METHOD AND MEANS FOR DETERMINING ULTRASONIC WAVE ATTENUATION IN TISSUE USING PHASE LOCKED LOOP

This invention relates generally to ultrasonic diagnostic systems, and more particularly the invention relates to a method and means for determining ultrasonic wave attenuation in tissue by frequency analysis.

Ultrasonic diagnostic systems are known and commercially available for medical diagnostic purposes. See for example U.S. Pat. No. 4,172,386 for "Video A-Trace Display System for Ultrasonic Diagnostic System" and U.S. Pat. No. 4,204,433 for "Computerized Ultrasonic Scanner with Technique Select". The commercially available Datason ultrasound system of General Electric Company provides both real time and static images on a television display.

Briefly, such systems utilize sound transducers to transmit ultrasonic waves (e.g. on the order of several megahertz) into a patient and to receive reflected signals. By analyzing the reflected signals a quantitative assessment of physical tissue parameters can be obtained. Such parameters include frequency dependent signal attenuation, time of flight, signal scatter and refractive effects. While medical diagnosis through ultrasound signal analysis has been successful, physiological variations and sample error problems limit the accuracy of the measurements.

Tissue attenuation of ultrasonic energy in the range of one to ten megahertz is found to be approximately a linear function of frequency and depth and is normally expressed dimensionally in db's/cm/MHz. Different tissues and different lesions within a given tissue tend to have different attenuation coefficients, thus each can be characterized by determining this coefficient.

Heretofore, the attenuation coefficient has been usually measured directly by obtaining a signal sample at two different depths within the tissue and then taking and comparing the Fourier transform of the signals. Theoretically, the frequency dependence of the attenuation function is obtained by dividing one spectrum by the other. In practice, however, the spectrum obtained from the tissue scatter produces a noisy spectrum, and the spectrum or frequency shift is usually estimated. Further, the spectral estimates are difficult to make since if a sample is too short the spectral resolution is limited and if the sample is too long a spectral smearing occurs since the spectrum is changing with depth. Thus, the frequency dependent attenuation coefficient for tissue has been a limited and difficult measurement.

Disclosed in copending application Ser. No. 369,423 filed Apr. 19, 1982 now U.S. Pat. No. 4,441,368 is a method and an apparatus for determining tissue attenuation by determining the number of zero crossings of a reflected ultrasonic wave as a function of depth of reflection in the tissue. By comparing the number of zero crossings at one depth to the number of zero crossings at the second depth, a measure of attenuation in the tissue between the first depth and the second depth is obtained.

The present invention is directed to a method and an apparatus using a phase locked loop for providing a measure of signal attenuation. A transducer generated signal in response to a reflected ultrasonic wave is applied to one input of a frequency or phase detector. A second input signal is provided by a voltage controlled oscillator. The output of the phase detector is applied as a feedback signal to the voltage control oscillator to control the frequency thereof. By tracking the feedback control voltage, a measure of the mean frequency of the reflected ultrasonic wave, and consequently a measure of tissue attenuation, is obtained.

Accordingly, an object of the invention is an improved method of measuring tissue attenuation of ultrasonic waves.

Another object of the invention is apparatus for measuring the frequency and changes in the frequency of a reflected ultrasonic wave.

A feature of the invention is the use of a phase locked loop to determine ultrasonic wave frequency.

The invention and objects and features thereof will be more readily apparent from the following detailed description and appended claims when taken with the drawing, in which one embodiment of apparatus for implementing the invention is illustrated.

Referring now to the drawing, ultrasonic waves 10 reflected from a patient or object under examination are received by a transducer 12 which generates an electrical signal in response thereto. As above described, the electrical signal from transducer 12 has a frequency on the order of several megahertz with the frequency of the electrical signal decreasing with attenuation of the ultrasonic wave and depth of reflection of the ultrasonic wave. The electrical signal is amplified by amplifier 14 and is conventionally applied to signal processing and display circuitry, as indicated, for viewing and analysis by a system operator.

In accordance with the invention, the electrical signal from amplifier 14 is applied through a frequency divider 16 to one input of phase detector 18. The frequency divider 16 may not be required but in view of the high frequency of the electrical signal from amplifier 14 (e.g. several megahertz) a stepdown in frequency for purposes of phase detection is desirable. The phase detector is a conventional circuit having two inputs and an output which can be used to control a voltage controlled oscillator to effect a phase lock of two input signals. A voltage control oscillator 20 provides the second input signal to phase detector 18, and the output of the phase detector 18 is applied through a voltmeter 22 to the control terminal of the voltage control oscillator 20. Accordingly, the frequency of the output signal from the voltage control oscillator 20 is controlled by the feedback from the phase detector 18 until the frequency of the signal from the voltage control oscillator 20 is the same as and in phase with the signal derived from amplifier 14.

By monitoring the magnitude of the voltage from the phase detector 18 as applied to the control terminal of voltage controlled oscillator 20, a measure of attenuation is obtained. The variation in voltage as a function of time is analogous to the decrease in frequency (and increase in signal attenuation) of the ultrasonic signal as a function of depth in the patient or body under examination.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. In an ultrasound imaging obtaining system, a method of a measure of attenuation of an ultrasonic wave comprising the steps of
   (a) providing transducer means for receiving reflected ultrasonic waves and generating an electrical signal in response thereto,
   (b) providing a phase detector having a first input terminal for receiving a first signal and a second input terminal for receiving a second signal and an output terminal, said phase detector generating an output signal on said output terminal which is indicative of the phase difference between said first and second signals,
   (c) connecting said electrical signal to said first input terminal,
   (d) providing a voltage controlled oscillator having an output terminal for a generated oscillation signal and a control terminal for receiving a signal for controlling oscillation frequency,
   (e) connecting said output terminal of said phase detector to said control terminal and applying said output signal of said phase detector for controlling oscillation frequency,
   (f) connecting said generated oscillation signal to said second input terminal of said phase detector and,
   (g) measuring the voltage of said output signal of said phase detector as indicative of attenuation.

2. The method as defined by claim 1 wherein step (c) includes the step of reducing frequency of said electrical signal.

3. The method as defined by claim 1 wherein step (g) is carried out over a period of time to measure frequency shift and attenuation at various depths of a body being examined.

* * * * *

UNITED STATES PATENT AND TRADEMARK OFFICE
CERTIFICATE OF CORRECTION

PATENT NO. : 4,546,772
DATED : October 15, 1985
INVENTOR(S) : Stephen W. Flax

It is certified that error appears in the above-identified patent and that said Letters Patent is hereby corrected as shown below:

Claim 1, lines 1 and 2, "In an ultrasound imaging obtaining system, a method of a measure of attenuation" should read -- In an ultrasound imaging system, a method of obtaining a measure of attenuation --.

Signed and Sealed this

Twenty-eighth Day of January 1986

[SEAL]

Attest:

DONALD J. QUIGG

Attesting Officer

Commissioner of Patents and Trademarks